(12) United States Patent
Unetich (10) Patent No.: US 9,802,057 B2
(45) Date of Patent: Oct. 31, 2017

(54) UNIVERSAL DIATHERMY HEAT APPLICATOR

(71) Applicant: Robert M. Unetich, Pittsburgh, PA (US)

(72) Inventor: Robert M. Unetich, Pittsburgh, PA (US)

(73) Assignee: Viatherm Therapeutics LLC, Annapolis, MD (US)

( * ) Notice: Subject to any disclaimer, the term of this patent is extended or adjusted under 35 U.S.C. 154(b) by 730 days.

(21) Appl. No.: 14/283,447

(22) Filed: May 21, 2014

(65) Prior Publication Data

US 2014/0350646 A1 Nov. 27, 2014

Related U.S. Application Data

(60) Provisional application No. 61/826,169, filed on May 22, 2013.

(51) Int. Cl.
*A61N 1/40* (2006.01)

(52) U.S. Cl.
CPC .................... *A61N 1/403* (2013.01)

(58) Field of Classification Search
CPC ............ A61N 1/40; A61N 1/403; A61F 7/007
USPC ......... 600/14–15; 607/101–103, 48
See application file for complete search history.

(56) References Cited

U.S. PATENT DOCUMENTS

| | | | |
|---|---|---|---|
| 4,527,550 A | 7/1985 | Ruggera | |
| 5,099,840 A | 3/1992 | Goble | |
| 5,160,828 A * | 11/1992 | Olsen | A61F 7/007 219/211 |
| 6,094,599 A * | 7/2000 | Bingham | A61N 1/36014 607/149 |
| 6,463,336 B1 * | 10/2002 | Mawhinney | A61N 1/40 600/14 |
| 6,853,865 B2 * | 2/2005 | Beens | A61N 1/403 600/15 |
| 7,979,139 B2 | 7/2011 | Beens | |
| 2005/0222642 A1 * | 10/2005 | Przybyszewski | A61N 1/0551 607/48 |
| 2006/0119462 A1 * | 6/2006 | Beens | A61N 1/403 336/200 |
| 2010/0036369 A1 | 2/2010 | Hancock | |
| 2011/0060391 A1 * | 3/2011 | Unetich | A61N 1/403 607/101 |
| 2011/0245900 A1 * | 10/2011 | Turner | A61N 1/403 607/100 |
| 2012/0265277 A1 * | 10/2012 | Unetich | A61F 7/007 607/101 |

\* cited by examiner

*Primary Examiner* — Albert Wong
(74) *Attorney, Agent, or Firm* — Leslie R. J. Virany (57) ABSTRACT

A resonant radio frequency diathermy heat applicator, including a flexible pad, an inductive coil with moderate defined resistance, fixed tuning capacitors, connecting cable and shielding that is broadly tuned to the signal source in a manner that eliminates the requirement for variable tuning elements.

20 Claims, 8 Drawing Sheets

UNIVERSAL DIATHERMY HEAT APPLICATOR

BACKGROUND OF THE INVENTION

The present invention relates to radio frequency diathermy application systems and devices.

Resonant Shortwave Diathermy Heat Applicators have been in use for a long period. Most employ a coil in parallel with a resonating variable capacitor and a coupling means. Radio Frequency (RF) coil systems have been used to apply heat to various portions of a patient's body, including limbs. Such systems have provided therapeutic medical treatment, including muscle healing, wound healing, and warming of hypothermia victims.

DESCRIPTION OF RELATED ART

A coil in parallel with a resonating variable capacitor and a coupling means to allow the resonant circuit to be efficiently connected to a low impedance signal source, as in U.S. Pat. No. 6,094,599 issued in July of 2000. The coil radiates the target tissue with energy in the form of both electric and magnetic fields, which cause currents to flow in perfuse tissue. Resistive losses in this tissue causes warming.

For example, U.S. Pat. No. 4,527,550 describes a coil designed for use under full-wave operation at coil-wire length resonance. This system is limited to operation in an electromagnetic shielded room in order to meet FCC requirements. U.S. Pat. No. 5,160,828 describes an apparatus for warming the extremities of a subject so that the subject can perform certain tasks in a cold environment. This apparatus can be operated in free-space, without shielding, while complying with environmental regulations.

U.S. Pat. Nos. 6,094,599, and 6,853,865 (the disclosures of each of which are expressly incorporated herein in their entirety by reference for purposes of essential subject matter), each disclose RF diathermy apparatus for warming the extremities of a subject, including, for example, a hand, wrist, forearm, elbow, ankle, and/or knee. Such apparatus may also be operated in free-space, without shielding, while complying with environmental regulations. These devices may be used for treating slow or non-healing wounds due to vascular inefficiency, diabetic peripheral neuropathy, microangiography, microvascular disease, or compression neuropathies such as Carpal Tunnel Syndrome. However, prior apparatus for application of RF diathermy have been substantially cylindrical in shape, or have required additional materials such as towels to provide for safe operation on large substantially planar muscle groups within the body, including, for example, the back, abdomen, chest, and/or neck areas. The absence of the additional material could result in overheating of the patient's subcutaneous fat layers and ultimately discomfort and injury.

BRIEF SUMMARY OF THE INVENTION

We propose that a new heat applicator design that provides rather consistent body area coverage and which includes the correct internal non-adjustable tuning components be designed. The product to be designed would include shielding to protect the coil incidental radiation, a balun to minimize conducted radiation and internal capacitors of values to eliminate the need for tuning when properly placed over a body surface.

DETAILED DESCRIPTION OF THE INVENTION

In a highly-preferred embodiment (as presented in FIGS. 1 & 2) a new heat applicator design that relies on rather consistent body area coverage and which includes the correct internal non-adjustable tuning components is designed.

The applicator supply circuit of the present invention needs to be accurately resonated, usually to allow more than 90% of applied energy to be absorbed, even when the target tissue, such as an arm or leg joint, happens to move. This typically changes the stray capacitance and detunes the network, which reduces the stored energy in the network and the electromagnetic field strength. The space between the patient ("target tissue") and the applicator creates this stray capacitance as electrostatic or quasi-static storage along the length of the coil. As is known in the art, the capacitance between two 'plates' or surfaces is inversely-related to the separation between them. Effectively a differential capacitance is set up along the entire length of the applicator wire. As this distance may range widely through an order of magnitude or so, the capacitance anywhere along the wire may do the same, as the patient moves, perhaps imperceptibly. At times, bearing weight on an area, this distance may be less than a millimeter, limited only by the resilience of the applicator foam or other spacer material. At others, a gap may be created of 10 times this distance or more. Detuning reduces tissue heating and the user must retune the network.

This invention involves using a high resistivity wire for the inductor, such as nickel or steel, in place of the normally highly conductive inductive circuit element. This modifies the circuit characteristics sufficiently to maintain a near resonant circuit under widely varying external conditions. A secondary benefit is that heat dissipated in the resistive wire provides incidental heat to the target tissue.

Figure 1:
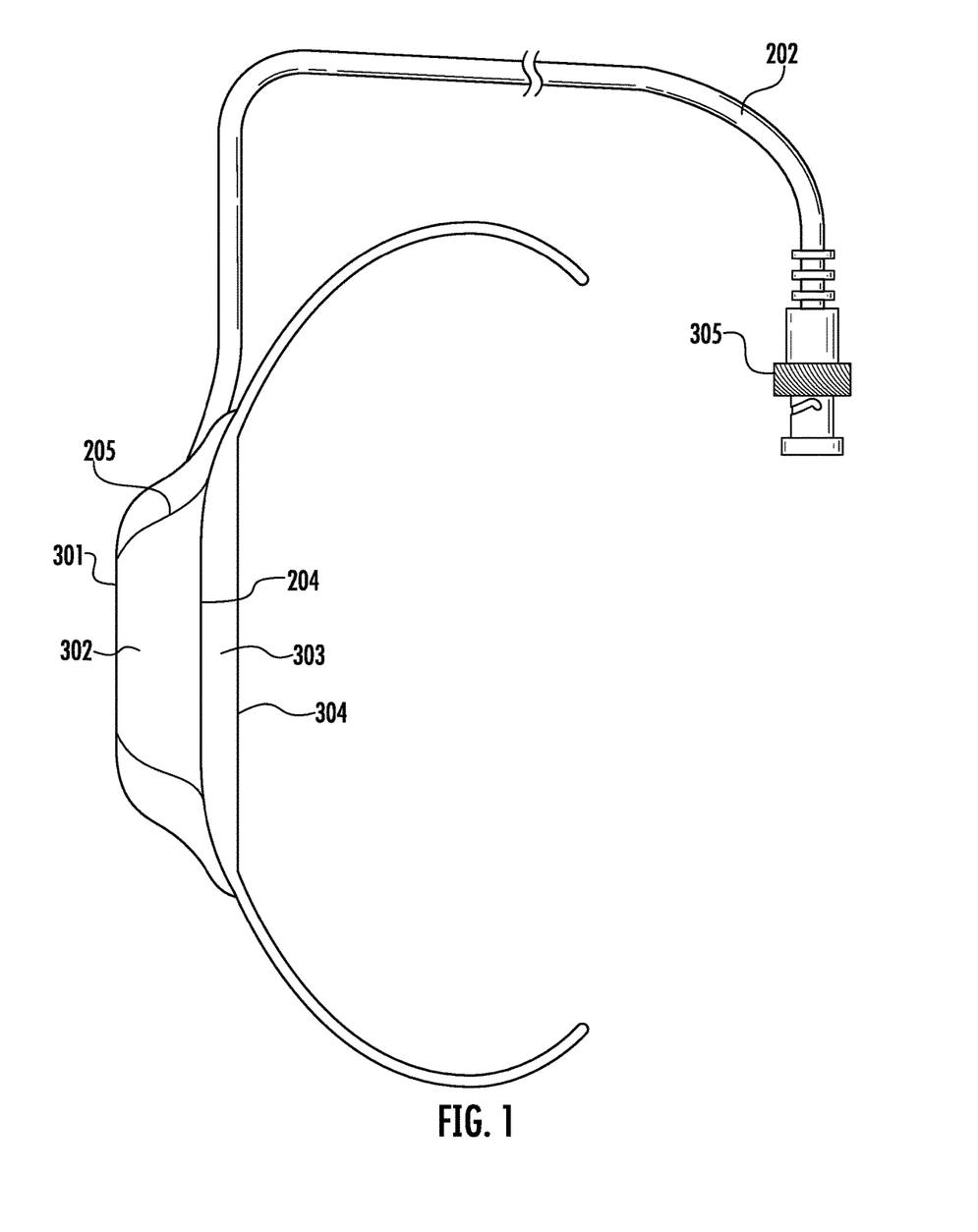
FIG. 1 Side View of the present invention
FIG. 2 See-Thru Back View of the invention of FIG. 1
FIG. 3 Diathermy Heat applicator schematic diagrams with external target tissue.

FIG. 1 shows a side view, with top fabric 301, shield 205, firm foam spacer 302, heating coil 204, soft foam spacer 303, bottom fabric 304, connector 305

Figure 2:
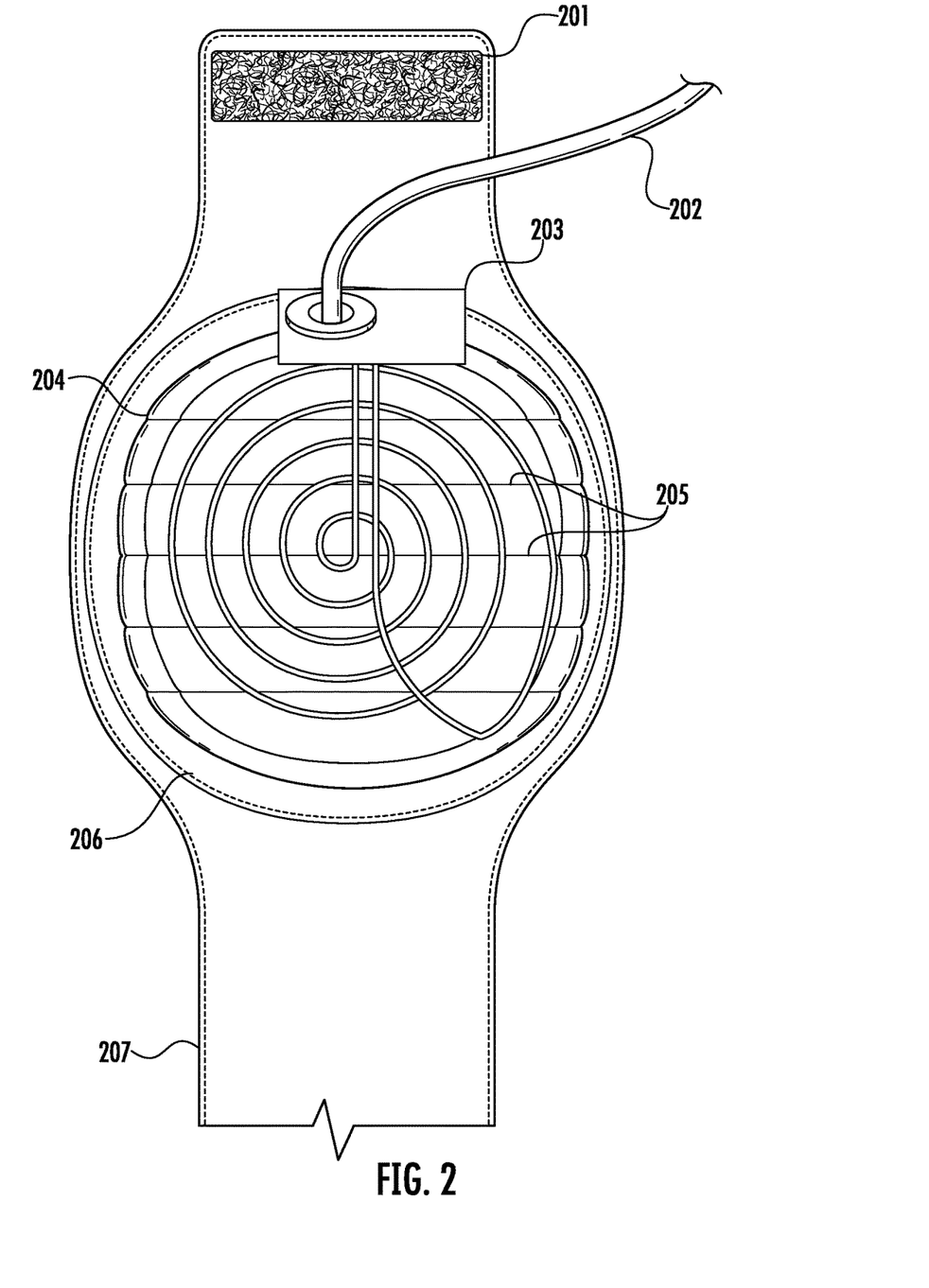

FIG. 2 gives a see-thru back view, showing Velcro (in an embodiment) hook material 201, coaxial cable connected to generator 202, impedance-matching electronics network 203, pseudo-spiral heating coil 204, shielding grid mesh 205, top-covering and foam spacers stitched 206, belt extension to Velcro (in an embodiment) pad end 207

Figure 8:
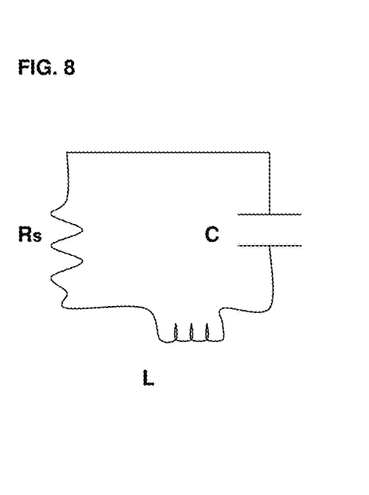

A resonant circuit, as shown below in figure one, has two reactive elements, an inductor, provided by coil inductance, and a capacitor, provided by circuit capacitance. Additionally there is also in series an effective resistance, Rs, that can be considered a combination of inherent total internal circuit resistance and radiation resistance, a parameter determined by how effectively the electromagnetic fields couple into surrounding objects and into free space.

Figure 9:
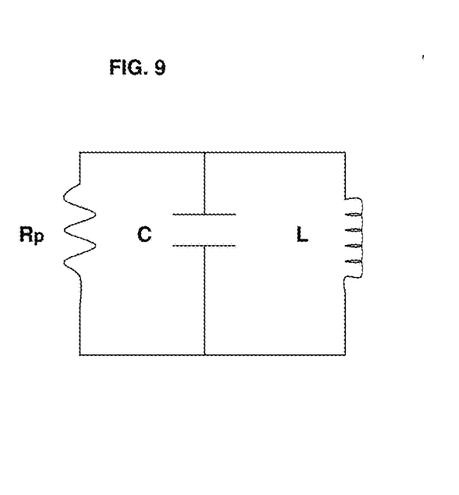

Although the circuit in figure eight is a series connected network, an equivalent parallel combination of inductance, capacitance and an effective parallel resistance is another way to visualize this circuit, as shown in figure nine. In this version it is obvious that external partially conductive objects, both capacitively and inductively coupled to the network, such as human limbs, can "load" the network. With no external target load, the "unloaded" network has an effective parallel resistance Ru. When the load is present, it is in parallel with Ru and the circuit has a net parallel loaded resistance at resonance of Rl.

In any parallel resonant circuit, the sharpness of tuning can be viewed as circuit "Q" (for Quality Factor), commonly defined as the magnitude of the inductive reactance, $\omega_l$, divided by the effective parallel resistance, Rp or $$Rp/\omega_l=0$$

The literature shows that this is also equivalent to the resonant center frequency, $f_c$, divided by the 3 dB bandwidth, $f_{3dB}$ or $$Q=f_c/f_{3dB}$$

In a resonant diathermy heat applicator, therefore Rp varies with the load and the Q varies from a maximum value of Qu $$Ru/\omega_l=Qu \text{ when unloaded,}$$

to Ql $$Ru/\omega_l=Ql \text{ when loaded,}$$

where Ru is the parallel resistance with no external load and Rl is the value with an external load.

If we modify Ru by reducing its value (i.e. when we "load" it more heavily), Qu and Ql will be reduced accordingly. In the series equivalent version of the circuit, this is equivalent to adding series inherent resistance to the circuit, increasing Rs. The total series resistance will increase further when loaded by the target, changing Q $$\omega l/Rs=Q$$

and its value depends on how heavily loaded the circuit is by nearby target tissue and by how much series resistance is added to the coil.

As previously stated, resonance is achieved by resonating the inductive reactance with the required value of capacitive reactance. It can be seen that the capacitance across the inductor is a combination of installed capacitors and any incidental stray capacitance across the circuit. When target tissue is brought sufficiently close to the coil to have currents flow in it, these currents are caused by both magnetic induction of eddy currents inn the tissue and by direct capacitive coupling of current caused by the strong electric field present at resonance.

Since the capacitively coupled external current adds capacitance across the coil that is not present when the applicator is unloaded, this changes the net circuit capacitive reactance of the network and this changes the resonant frequency. When the network center resonant frequency moves well away from the frequency of the signal generator supplying radio frequency power, heat therapy is reduced. Typically, the network can maintain sufficient effective heating when the network remains accepts 90%, reflecting 10%. When the network detunes beyond this point, external circuits normally sense the condition (SWR>2:1) and disable the source signal. It may also alert the operator that the applicator requires retuning.

When series resistance is added to the coil, the bandwidth is increased and if sufficient resistance is added, the stray capacitance effects will not be sufficient to move the network beyond its 10% reflected power bandwidth.

With the proper combination of resistance and fixed external tuning capacitance, the network will operate with no load or with a very heavy load and the need for retuning during heat therapy has been eliminated. Tests demonstrate that this combination can be achieved and a new product line of resonant diathermy heat applicator can be designed that require no operator tuning. The typical assembly that employs this technique is fully described below.

A typical resonant diathermy heat applicator has 6 to 7 microhenrys of inductance, which requires about 25 picofarads of capacitance to resonate at 13.56 MHz, a common operating frequency. In practice, this circuit may have an equivalent series resistance at resonance of 15 to 65 ohms, depending on external loading. This resistance includes both intrinsic circuit resistance that further has skin effect characteristics and "radiation resistance" causes by both incidental radiation away from the target and the direct loading effect of the target tissue.

The resistance range is rather large because of the high variability of the loading effect of the target tissue. With no target present, the radiation resistance component will be low, usually about 15 ohms. A heavily loaded unit (i.e. a unit tightly coupled to a large target area of tissue, will have fairly high resistance, usually around 50 ohms or above.

Figure 3:
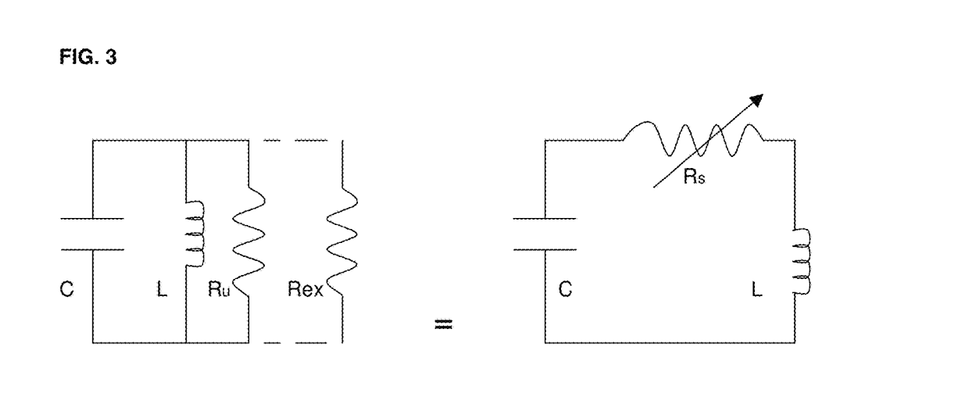

The result, as given by the schematic in FIG. 3, (Diathermy Heat applicator schematic diagrams with external target tissue:) is a new applicator that remains sufficiently near resonance to operate with any external load or no load at all. The added series resistance does increase internal thermal heating of the coil but this heat also warms the surrounding tissue and contributes to the heat therapy component of diathermy.

The resistance necessary to achieve this broadening of the bandwidth is about 5 ohms of DC resistance and this value can be added in series as a discrete component or incorporated in the coil design by using highly resistive wire such as nickel or other high resistivity materials. In a preferred embodiment the optimal added resistance is about 6 ohms. Skin effect at the operating frequency further increases this effective resistance with the objective being that the operating bandwidth never drops below about 2%. This allows sufficient margin to account for normal changes in external stray capacitance. The source impedance is typically 50 ohms, especially in the region of interest The two plots of FIG. 4, below illustrate these effects. The plots are of the input return-loss of a standard applicator that employs copper coil conductor and of a unit assembled with nickel wire as the inductor, which exhibits about five ohms of Dc resistance in this implementation. The first plot has markers at the desired operating frequency, 13.56 MHz, and at points shown in the table. Markers 4 and 5 are approximately at the 2:1 SWR point or the operating limits of this unit, which shows an operating bandwidth of 124 kHz.

Figure 4:
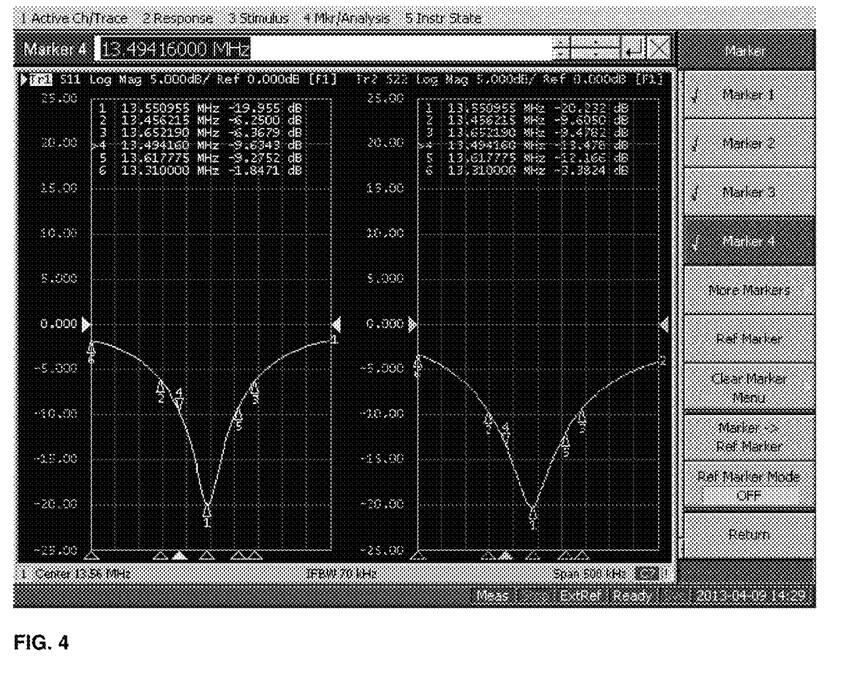
FIG. 4 Plots of the input return-loss of the invention (right) compared with a standard applicator (left)
FIG. 5 Side view
FIG. 6 Coil Winding Procedure
FIG. 7 Schematic showing Impedance Matching Network
FIG. 8 a series resonant network $Q=\omega_l/R_s$
FIG. 9 a parallel equivalent $Q=R_p/\omega_l$

The second plot has a 2:1 SWR of about (markers 2 and 3) 196 kHz or 58% greater, sufficient to maintain the 2:1 SWR requirement with any normal change in external stray capacitance, making this diathermy heat applicator a novel fixed tuned design superior to previous resonant diathermy applicators. The required resistance of the new applicators, achieved by using an appropriate high resistivity wire or by simply adding a suitable fixed resistance to a more conductive wire coil, insures the resonant circuit will have a bandwidth sufficiently wide to make precise tuning unnecessary.

In practice, the addition of about six ohms in series with the coil inductance has been shown to work well although values from four to eight ohms also are functional. This has been done with coil inductances ranging from several micro-henries to ten micro-henries and an excellent compromise value of 6.5 micro-henries has performed well. Using this value, a standard resonant diathermy applicator has a load impedance of about 15 ohms, which represents a standing-wave-ratio (SWR) of 50/15~3.3:1. This value can also be referred to as a 6 dB return-loss, which is a 25% reflected power. Improving the SWR to under 2:1 increases the return-loss to better that 10 dB, indicating that less than 10% of delivered RF power is reflected back to the generator. The 2:1 SWR limit is usually established as the upper limit of reflected power and therefore can be selected as a criteria for acceptable diathermy heat applicator operation. Adding the six or so ohms of series resistance increases the equivalent series load impedance of an unloaded applicator to over 20 ohms (skin effect adds some additional resistance over the DC value) and as soon a very light target load gets near the applicator, the additional loading moves the load impedance to above 25 ohms, reducing the SWR to under 2:1. This permits the generator to operate within its acceptable load range.

Referring to the return-loss curves shown in FIG. 4, note that marker 2 and marker 3 in the photo are approximately 100 kHz away from the nominal operating frequency of 13.56 mHz. In actual practice, movement by the target tissue, commonly caused by any movement by a person using diathermy applicators, causes stray capacitance to change along with effective loading resistance. This can cause a heat applicator to move in resonant frequency as much as 100 kHz. In previous designs (as shown on the first plot) this will cause the return-loss to change to about 6 dB (a 3:1 SWR). The new version maintains a return-loss of over 10 dB (SWR<2:1) with the same 100 kHz shift in resonant frequency, as seen on the second plot, because of the lower Q.

Overall applicator area can vary significantly if these coil characteristics are maintained. A six square inch spiral coil using eighty inches of 0.025-inch diameter nickel wire was built with 6.2 micro-henries of inductance and 6.3 ohms of resistance. Using wire of twice the cross sectional area, a large spiral with a ten inch diameter and 150 inches of wire length was built and it had just under 6 micro-henries of inductance and 5.9 ohms of resistance and both produced acceptable SWR reading of under 2:1 and therefore worked well accepting RF power. In each case, the radio frequency power applied was adjusted in proportion to effective area to achieve the same RF power density of radiated power, which in practice is about 100 milliwatts per square centimeter, and the resulting tissue heating was in the normally acceptable range for diathermy treatments.

As noted, the resistance can be achieved with different wire materials and with added fixed resistance if desired. Another coil of 80 inches on length of copper was wound to achieve six micro-henries of inductance and a six ohm fixed power resistor was added in series to achieve the desired DC resistance and this unit tuned in an identical manner.

Figure 5:
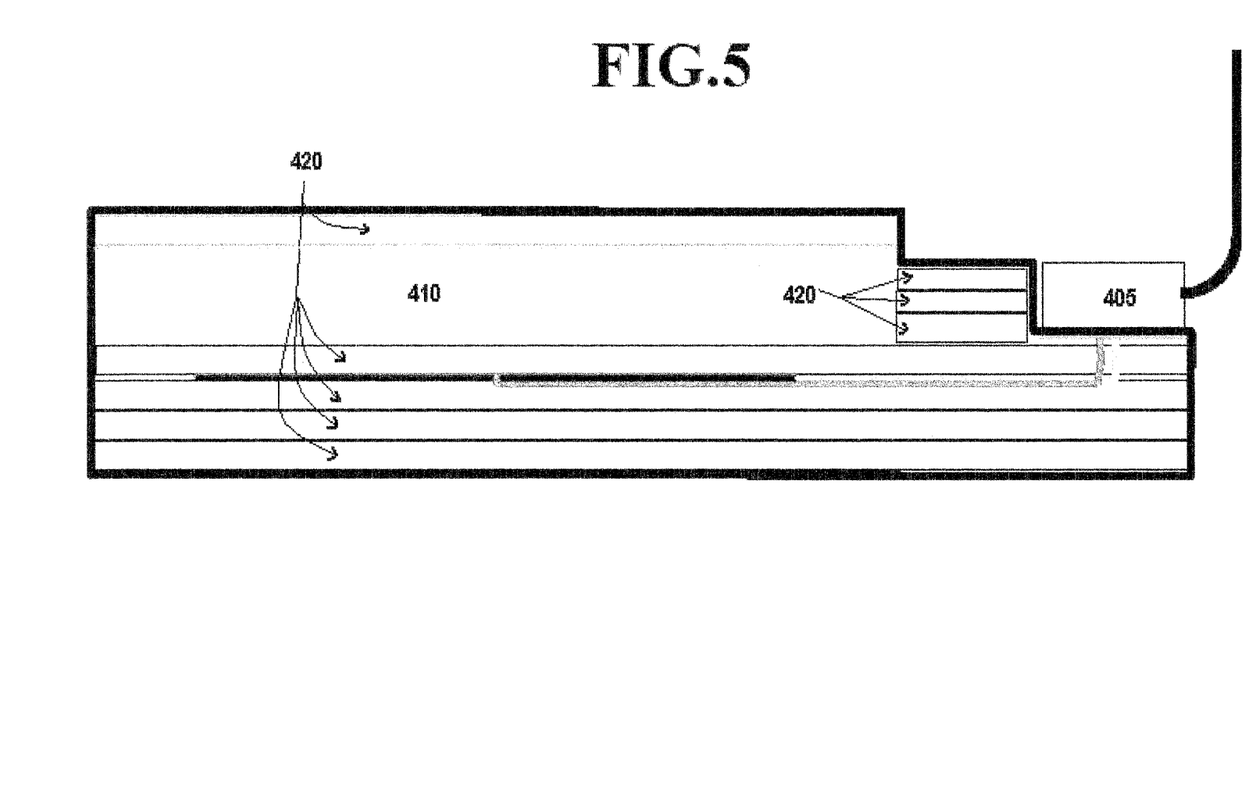

FIG. 5 presents a side view showing Impedance Matching Network 405, Shield Spacer1.0" Hard Foam layer 410 and 375" soft foam layers 420 is given in FIG. 5.

Coils can be wound from wire or printed on suitable substrates such as the polyimide film known as Kapton. Printed line lengths, thicknesses and conductivities would be adjusted to achieve the desired inductance and resistance. With the above selection of characteristics, the load impedance presented to the source signal remained within the acceptable range for the generator utilized. Other generators with different mis-match capabilities could be used if the Q of the diathermy applicator was established using the above techniques to permit safe operation.

Figure 6:
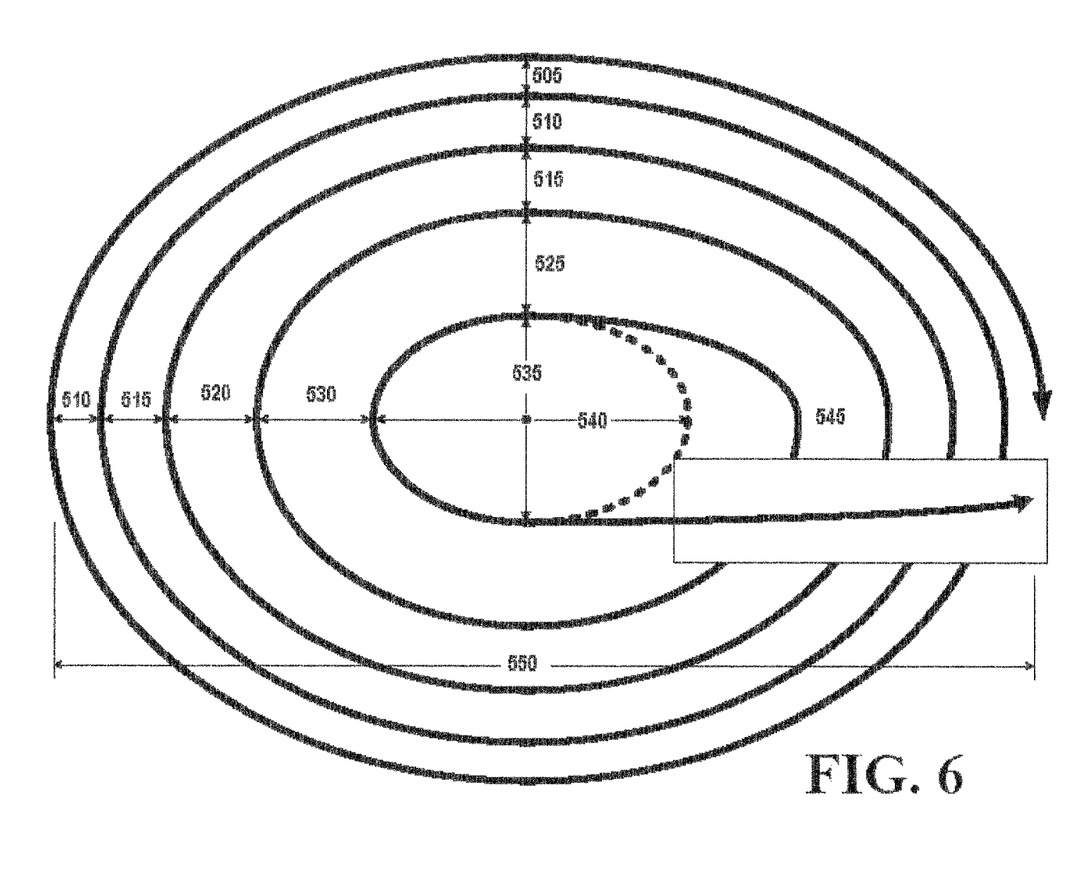

FIG. 6 illustrates the coil winding procedure, the best spatial winding pattern for achieving uniform application of RF energy in the preferred embodiment of a universal applicator usable either as a limb wrap or a surface such as, but not limited to, an area of a subject's back. Measurements indicated, in inches, are respectively 505 0.375, 510 0.5, 515 0.625, 520 0.875, 525 1 530 1.125, 535 2, 540 3, 545 7.5, 550 10.

Figure 7:
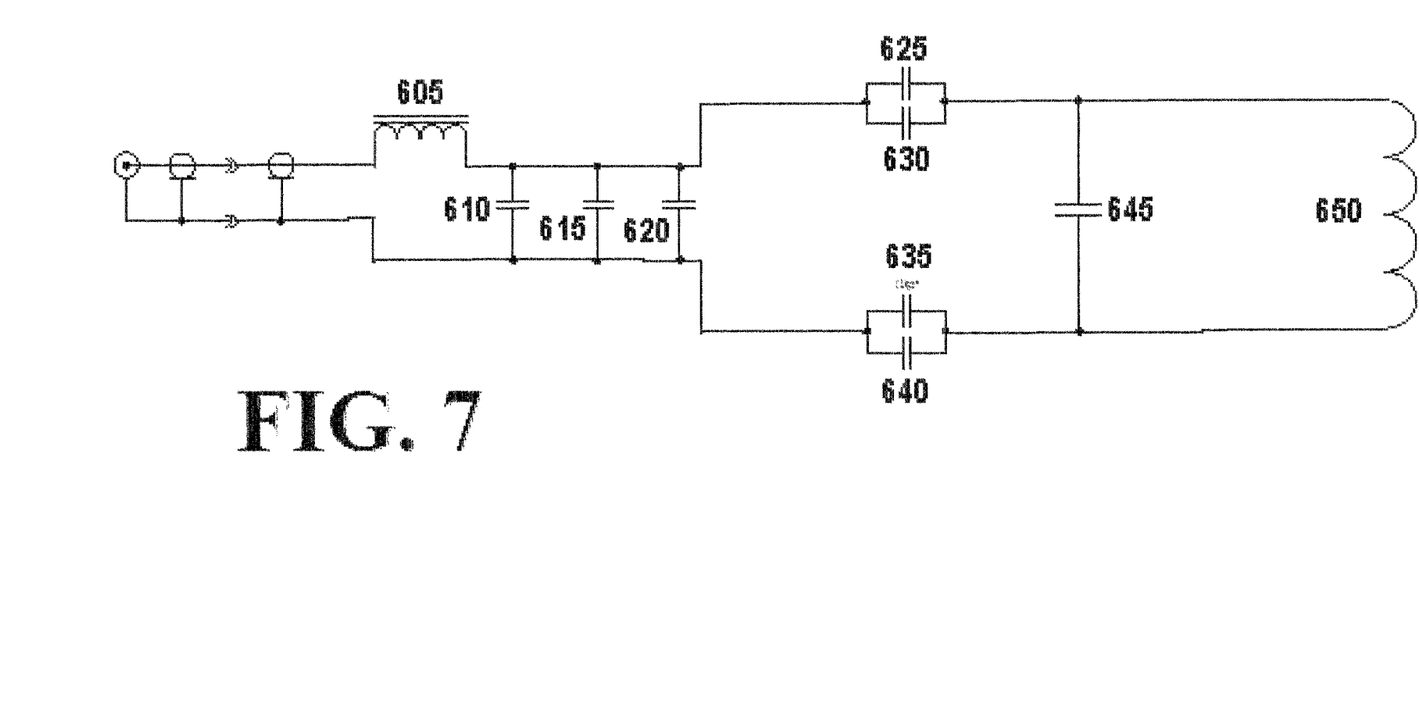

FIG. 7 is a schematic showing Impedance Matching Network where L2 is the coil applicator. 605 L1 610 C1 47 pF 615 C2 47 pF 620 C3 47 pF 625 C4 12 pF 630 C5 10 pF 635 C6 10 pF 640 C7 12 pF 645 C8 10 pF 650 L2

Figure 10:
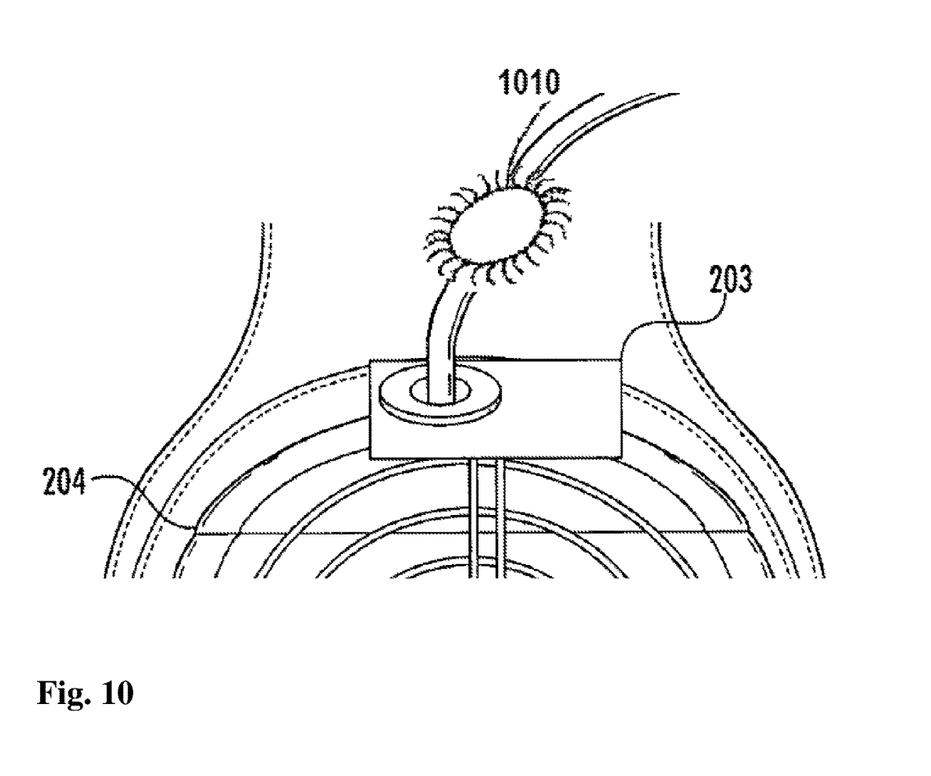
FIG. 10 shows a detail of an embodiment of the applicator of FIG. 2, including a balun

The product to be designed would include shielding to minimize incidental radiation, a balun 1010 to minimize conducted radiation and internal capacitors of values to eliminate the need for tuning when properly placed over a body surface larger than the effective heating target.

The area to be treated is proposed to be between 30 and 40 square inches and the operating power of the applicator is expected to be approximately 18 watts or about 50% of the RE-100 power capability. This reduced area would make matching a body part, such as an arm or leg or back, much more uniform and by using lower power, the effective heating would be approximately the same while incidental radiated power would be reduced. The smaller size would also allow an effective shield, fabricated to be larger than the heating area, to be included and this size relationship would contribute significantly to the reduction in extraneous radiation.

The shape of the proposed heating coil would be approximately be a spiral although we would use the techniques of the above-incorporated references to make heating uniform over the area of tissue being treated. The design would include a pre-formed plastic form to allow east wrapping of limbs but also allow the treatment of a flat lower back area.

The smaller size, lack of variable capacitor and small shield will contribute to low manufacturing cost.

Many modifications and other embodiments of the disclosure will come to mind to one skilled in the art to which this disclosure pertains having the benefit of the teachings presented in the foregoing descriptions and the associated drawings.

For example, fasteners such as Velcro have known equivalents and may be attached different ways, cables and fabrics depicted may be substituted with equivalents and mechanical hardware such as screws and rivets are known to reducible to practice in a variety of ways.

Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

What is claimed is:

1. A diathermy applicator for delivering controlled heating treatment to capacitively- and inductively-coupled patient target tissue comprising;

a coil assembly comprising an inductive coil of wire characterized by a coil inductance and a coil resistance a source of RF power a load characterized as a parallel resistance comprising said coil resistance and a radiation resistance, said radiation resistance exhibiting variance and comprising said capacitively- and inductively-coupled patient target tissue a fixed tuning circuit capacitance determining, along with said coil inductance, an unloaded electromagnetic resonant frequency $\omega_l$ effecting a reactive impedance matching of said RF power to said patient target tissue wherein;

said applicator is characterized by a Q or "quality factor" curve, dependent on said parallel resistance and having a resonant bandwidth throughout which said reactive impedance matching is maintained, said load is further characterized as an equivalent series resistance as seen from said source of RF power, which comprises a series equivalent of said parallel load resistance in series with an added resistance said variance detunes said reactive impedance matching spontaneously during delivery of said controlled heating, said added resistance is selected so as to broaden said resonant bandwidth so as to maintain said reactive impedance matching throughout said treatment.

2. The diathermy applicator of claim 1 wherein said equivalent series resistance at resonance ranges from approximately 15 to 65 ohms, during said detuning.

3. The diathermy applicator of claim 1 wherein said added resistance is added to the coil assembly by choosing a higher resistivity wire for said inductive coil.

4. The diathermy applicator of claim 1 wherein said added resistance is added by connecting a discrete resistor in series with said coil.

5. The diathermy applicator of claim 2 wherein said added resistance comprises DC resistance in the range of 4-8 ohms.

6. The diathermy applicator of claim 3 wherein said higher resistivity wire comprises nickel or steel.

7. The diathermy applicator of claim 2 wherein the network maintains 90% effective heating when the network is subject to maximum detuning over a standard therapeutic heating delivery period of from 10-30 minutes.

8. The diathermy applicator of claim 5 wherein said fixed tuning circuit capacitance comprises about 25 pico-farads.

9. The diathermy applicator of claim 5 wherein said inductive coil of wire exhibits approximately 6 to 7 micro-henrys of inductance.

10. The diathermy applicator of claim 5 wherein the source of RF power has an impedance of approximately 50 ohms, when operated within said bandwidth.

11. The diathermy applicator of claim 5 wherein the added resistance is approximately 6 ohms.

12. The diathermy applicator of claim 7 wherein said coil comprises an approximately six square inch spiral coil using eighty inches of 0.025-inch diameter nickel wire having 6.3 ohms of resistance and inductance ranging from several micro-henries to ten micro-henries.

13. The diathermy applicator of claim 7 wherein said coil comprises an approximately ten inch diameter spiral having 150 inches of wire length, slightly less than 6 micro-henries of inductance and 5.9 ohms of resistance.

14. The diathermy applicator of claim 7 further comprising shielding surrounding said coil to minimize incidental radiation and a balun in parallel with said coil to minimize conducted radiation.

15. The diathermy applicator of claim 7 wherein said source of RF power has a capability in the neighborhood of three dozen Watts, the area to be treated is between about 30 and 40 square inches and the operating power of the applicator is approximately 50% of the source of RF power capability and wherein said area is a body part, such as an arm or leg or back.

16. The diathermy applicator of claim 7 further comprising a pre-formed firm foam spacer form to allow easy wrapping of limbs but also allow the treatment of a flat lower back area.

17. The diathermy applicator of claim 12 wherein said inductance is in the range of 6.2 to 6.5 micro-henries.

18. The diathermy applicator of claim 5 wherein the resonant frequency is approximately 13.56 MHz.

19. The diathermy applicator of claim 5 wherein the added resistance is approximately 6 ohms.

20. The diathermy applicator of claim 17 wherein said inductance is approximately 6.2 micro-henries.

* * * * *